US009226692B2

United States Patent
Haas

(10) Patent No.: US 9,226,692 B2
(45) Date of Patent: Jan. 5, 2016

(54) SYSTEM AND METHOD TO DETECT AND QUANTIFY LAMENESS IN ANIMALS

(71) Applicant: Clinical Image Retrieval Systems, Inc., Sparta, NJ (US)

(72) Inventor: Douglas D. Haas, Sparta, NJ (US)

(73) Assignee: Clinical Image Retrieval Systems, Inc., Sparta, NJ (US)

( * ) Notice: Subject to any disclaimer, the term of this patent is extended or adjusted under 35 U.S.C. 154(b) by 182 days.

(21) Appl. No.: 14/094,200

(22) Filed: Dec. 2, 2013

(65) Prior Publication Data

US 2014/0155785 A1 Jun. 5, 2014

Related U.S. Application Data

(60) Provisional application No. 61/733,248, filed on Dec. 4, 2012.

(51) Int. Cl.
*A61B 5/00* (2006.01)
*A61B 5/103* (2006.01)

(52) U.S. Cl.
CPC ........... *A61B 5/1038* (2013.01); *A61B 2503/40* (2013.01)

(58) Field of Classification Search
CPC ........ A61B 5/11; A61B 5/112; A61B 5/1123; A61B 5/1038
USPC ...................................................... 600/595
See application file for complete search history.

(56) References Cited

U.S. PATENT DOCUMENTS

| 4,647,918 | A | * | 3/1987 | Goforth | 340/573.1 |
|---|---|---|---|---|---|
| 5,299,454 | A | * | 4/1994 | Fuglewicz et al. | 73/172 |
| 5,474,087 | A | * | 12/1995 | Nashner | 600/595 |
| 6,231,527 | B1 | * | 5/2001 | Sol | 600/595 |
| 7,231,834 | B2 | * | 6/2007 | Kurono | 73/800 |
| 7,467,603 | B2 | * | 12/2008 | Davies | 119/712 |
| 8,002,672 | B2 | * | 8/2011 | Brunner | 482/8 |
| 8,147,430 | B2 | * | 4/2012 | Abdullah | 600/592 |
| 8,382,687 | B2 | * | 2/2013 | Lepine et al. | 600/595 |
| 8,639,455 | B2 | * | 1/2014 | Horst et al. | 702/44 |
| 8,790,279 | B2 | * | 7/2014 | Brunner | 600/595 |
| 8,845,494 | B2 | * | 9/2014 | Whitall et al. | 482/8 |
| 9,072,930 | B2 | * | 7/2015 | Ashby et al. | |

* cited by examiner

*Primary Examiner* — Max Hindenburg

(74) *Attorney, Agent, or Firm* — Hoffmann & Baron, LLP

(57) ABSTRACT

Provided is a method, system and computer readable-medium to evaluate lameness in a four-legged animal. The method includes selecting a gait analysis test. Test data associated with the animal is collected for a plurality of gait cycles at a speed associated with the test. The test data is collected in relation to a pressure sensor pad having a plurality of sensors. A plurality of paws and associated paw pressure of the animal are identified in association with each of the cycles in relation to the sensor pad. A gait lameness score is computed in association with a paw based on a ratio of, a total paw pressure for the paw in the plurality of gait cycles divided by total pressure for the plurality of paws in the plurality gait cycles, and a mean paw pressure for the paw that is expected by a breed of the animal.

30 Claims, 6 Drawing Sheets

GAIT
LAMENESS
SCALE (GLS)

TOTAL PRESSURE INDEX (TPI)

SYSTEM AND METHOD TO DETECT AND QUANTIFY LAMENESS IN ANIMALS

CROSS REFERENCE TO RELATED APPLICATION

This application claims priority to and benefit of U.S. Provisional Patent Application No. 61/733,248 filed on Dec. 4, 2012, the disclosure of which is incorporated in its entirety by reference herein.

BACKGROUND

1. Field

The present application relates to gait analysis in animals. More specifically, the present application is directed to a system and a method of detecting and quantifying lameness in animals. The system and method also enable the display of detected and quantified lameness on various computing devices and smart devices to facilitate understanding by clinicians, as well as lay people (owners).

2. Brief Discussion of Related Art

Gait analysis is a term that is broadly used in evaluating mobility in humans and animals, and can refer to systems that typically look at a limited number of measures in evaluating such mobility. For example, a system that measures pressure in a shoe for a human can refer to gait analysis at one end of the spectrum, while a system that uses three-dimensional (3D) video with markers to record and measure kinematics can also refer to gait analysis at the other end of the spectrum.

Systems that imbed sensors in treadmills for use with human subjects have been around for many years, generally focusing on location data in order to determine foot placement of the human subjects. In recent years, these systems have also been combined with projection systems that show where the subjects should place their feet, in order to determine how well the subjects completed this task. The foregoing systems are useful in human rehabilitation.

However, the aforementioned systems that are directed to the evaluation of foot placement in humans are not very useful to the evaluation of lameness in four-legged animals, e.g., dogs. Evaluation of lameness in animals requires specific animal-related measurements including, among other measurements, the pressure that these animals put on their paws, placement position of the paws at one or more specific points during a gait cycle, and the timing among the paws at various velocities.

Several systems perform gait analysis in animals and provide some degree of lameness detection and evaluation, whether directly or through clinician interpretation. One such system employs a relatively short over-the-ground pad. A drawback of such a system is that it collects a limited number of paw prints based on the speed of the animal and the animal's overall size, thereby requiring multiple passes over the pad in order to collect enough data for the evaluation of the animal. These passes may not include complete consecutive gait cycles. Specifically, it is well documented that even a single gait cycle collected only once is not adequate to accurately determine a degree of lameness for both primary and secondary lameness in animals.

Another system uses a longer walkway (e.g., 16 feet-26 feet) to capture a minimum of three consecutive gait cycles. This system provides an adequate number of gait cycles to determine both primary and secondary lameness. However, a drawback of such a system is the space required to layout the walkway and the difficulty in collecting data over the longer walkway at a consistent velocity.

While 3D video systems that use markers can be employed to detect lameness, such video systems are capable of producing accurate results only if lameness in the animals is visually identifiable. However, animals (especially dogs) are masters at compensation that makes lameness detection problematical even using the 3D video systems with markers. Moreover, the time and space requirements associated with use of such systems in clinical settings present additional drawbacks.

Other devices, such as force plates and static pressure reading devices for lameness detection are well known. Force plates require elaborate test methods to identify which paw is being measured and do not collect complete gait cycles. Static devices are unable perform dynamic analysis that is required for primary and secondary lameness detection in individual animals.

The foregoing systems and devices are generally not capable of producing accurate scoring to allow objective evaluation and reporting of the degree of lameness and to enable the tracking of changes during and following treatment of the animals.

SUMMARY

In accordance with an embodiment, a system to evaluate lameness in a four-legged animal is disclosed. The system includes a processor and a memory. The memory stores instructions that, when executed by the processor, cause the processor to perform the following operations.

A gait analysis test associated with a test speed is selected. Gait-related test data are collected in association with the animal at the test speed for a plurality of gait cycles. The gait-related test data are collected in relation to a pressure sensor pad having a plurality of sensors.

A plurality of paws and associated paw pressure of the animal are identified in association with each of the gait cycles in relation to the sensor pad, from the gait-related test data. A gait lameness score associated with a paw is computed based on a ratio of, a total paw pressure for the paw in the plurality of gait cycles divided by total pressure for the plurality of paws in the plurality gait cycles, and a mean paw pressure for the paw that is expected by a breed of the animal.

In accordance with another embodiment, a method of evaluating lameness in an animal is disclosed. The method includes selecting a gait analysis test associated with a test speed. Gait-related test data associated with the animal are collected at the test speed for a plurality of gait cycles. The gait-related test data are collected in relation to a pressure sensor pad having a plurality of sensors.

A plurality of paws and associated paw pressure of the animal are identified in association with each of the gait cycles in relation to the sensor pad from the gait-related test data. A gait lameness score associated with a paw is computed based on a ratio of, a total paw pressure for the paw in the plurality of gait cycles divided by total pressure for the plurality of paws in the plurality gait cycles, and a mean paw pressure for the paw that is expected by a breed of the animal.

In accordance with a further embodiment, there is disclosed a computer-readable medium storing instructions that, when executed by a processor, cause the processor to perform the following operations for evaluating lameness in a four-legged animal.

A gait analysis test associated with a test speed is selected. Gait-related test data are collected in association with the animal at the test speed for a plurality of gait cycles. The gait-related test data are collected in relation to a pressure sensor pad having a plurality of sensors.

A plurality of paws and associated paw pressure of the animal are identified in association with each of the gait cycles in relation to the sensor pad, from the gait-related test data. A gait lameness score associated with a paw is computed based on a ratio of, a total paw pressure for the paw in the plurality of gait cycles divided by total pressure for the plurality of paws in the plurality gait cycles, and a mean paw pressure for the paw that is expected by a breed of the animal.

These and other purposes, goals and advantages of the present application will become apparent from the following detailed description of example embodiments read in connection with the accompanying drawings.

BRIEF DESCRIPTION OF THE DRAWINGS

Some embodiments are illustrated by way of example and not limitation in the figures of the accompanying drawings in which.

DETAILED DESCRIPTION

Figure 1:
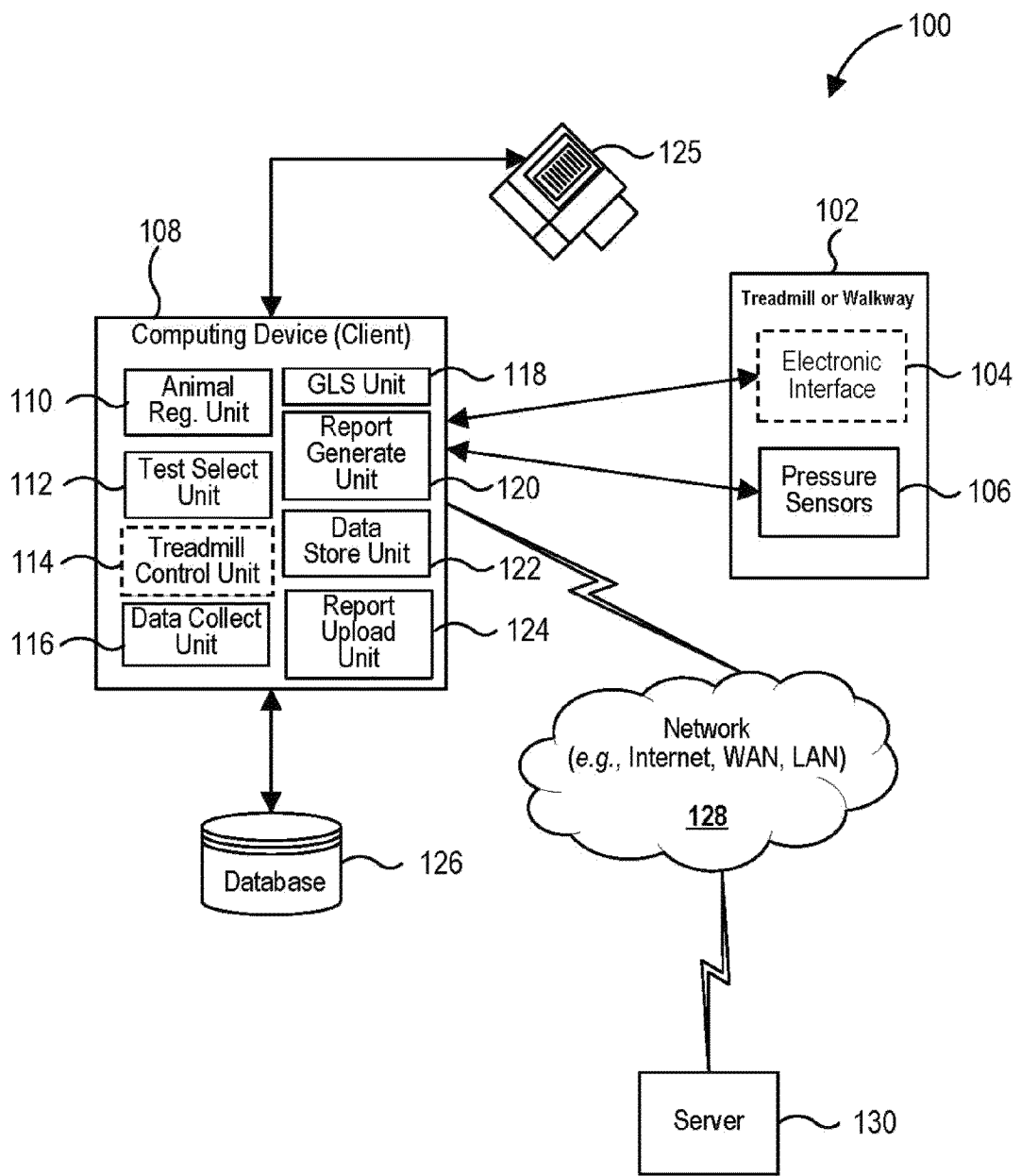
FIG. 1 illustrates an example system to detect and quantify lameness in animals.

A system and a method of detecting and quantifying lameness in animals are disclosed herein. In the following description, for the purposes of explanation, numerous specific details are set forth in order to provide a thorough understanding of example embodiments. It will be evident, however, to one skilled in the art, that an example embodiment may be practiced without all of the disclosed specific details.

The system and method are applicable to both treadmill-based and walkway-based animal lameness detection and quantification. The system and method can use pressure sensors embedded into any animal treadmill or ground-based walkway to provide pressure data, timing data and location data (gait analysis data), which can be combined with the individual dog breed and physical characteristics. While the system and method can be applied to various subjects (e.g., animals), it is specifically useful in evaluating dogs.

The system and method establish a scoring scale, aptly termed gait4dog lameness scale or GLS. The GLS represents a degree of off-loading (lameness) and over-loading (compensation) by a limb or leg of the animal, e.g., a dog. It is well known that dogs are adept at camouflaging their lameness. Thus, the GLS is a scale that accounts for appropriate off and over loading (pressure) and movement for each leg as to distance traveled and time spent. The scale reports on a curve were the further the limb is from the expected breed-based value (reported as 100%), the greater the respective lameness or compensation in that limb. The system and method use a number of variables derived from a combination of pressure data, timing data and location data collected while the animal is walking, pacing and/or trotting on the treadmill or walkway along with data about the animal such as its breed, height at shoulders and hip, body length and width at shoulders and hip.

The system and method are configurable to specific characteristics of the individual sensor pad (including a plurality of pressure sensors in a variety of pressure sensing technologies) embedded between the belt and bed of the treadmill or disposed inside the walkway. The sensor pad can be of any length and width depending on the size of the treadmill or the size of the walkway, and can provide different sensor density needed for differently-sized animals. The sensor pad provides data on the location, timing and pressure as the animal's paw makes contact with the belt and presses certain sensors in the sensor pad.

The method can be implemented on a computing device (e.g., a personal computer), a smart devices (e.g., Apple IPad, Android Smart pads, or another smart device). The method via the computing device can collect gait analysis data from an instrumented treadmill or walkway through a direct connection (e.g., Serial, USB, Fire Wire, etc.) or a wireless connection (e.g., Wi-Fi, Bluetooth, or another wireless connection). Moreover, the method via the computing device can simultaneously collect video data from one or more (preferably two or more) cameras (e.g., web cams or high speed video cameras). In the treadmill configuration, the system and method can communicate with the treadmill to control its functions (e.g., start, stop, speed, or another function) depending on the specific capabilities of the treadmill. In cases where the treadmill does not allow external control of its functionality, the system and method can instead prompt an operator (user) to manually control the treadmill, such as to start/stop the treadmill and the set required speed, etcetera. In the walkway configuration, the system and method can prompt an operator (user) to control the animal to walk, pace or trot along the walkway at the required speed. This can be achieved with training of the animal.

As already discussed hereinabove, there are systems in the marketplace that perform lameness detection using long over-the-ground pads. In contrast to these pads, the system and method enable accurate control of the treadmill speed (and necessarily the speed of the animal) or the speed of the animal along the walkway during testing, and combine the collected gait analysis data with data known about the specific breed of the animal. By collecting gait analysis data at several different speeds (e.g., walking, pacing and trotting) the GLS improves repeatability and accuracy of the lameness reporting for both configurations. The configurations using a treadmill or walkway as described herein provide the ability to collect a plurality of gait cycles (e.g., consecutive gait cycles) at certain speeds, which improves the accuracy and the granularity of the GLS. As used herein, a gait cycle is a sequence of four (4) paws as the subject (animal) walks, paces or trots. Accordingly, plurality of gait cycles is a sequence of gait cycles as the subject (animal) walks, paces or trots.

It should be noted, however, that the treadmill configuration introduces unique challenges in paw identification as well as proper data collection and sampling as compared to the over-the-ground walkway configuration. This configuration provides unique logic in contrast to the walkway configuration because the animal's paw slides over the stationary sensors as the treadmill advances during testing. The system and method implement a rules-based model that looks at each paw as it makes contact with the belt of the treadmill (and the pressure sensor pad), specifically tracking the paw from its first contact and until it breaks contact with the belt (and sensor pad). The model accounts for the fact that the animal is capable of placing the trailing hind paw under the rising forepaw. While paw identification is performed in real-time for most animals, sometimes post-collection processing with a look ahead may be required in order to distinguish where the hind paw begins and the forepaw ends.

The system and method can prompt the operator (user) concerning gait analysis tests (and related speeds) to be conducted for a given testing protocol for the treadmill and walkway configurations. Once a certain number of gait cycles (e.g., 4 paws set sequences) have been collected at a certain speed for a gait analysis test (e.g., walk, pace, or trot test), the system and method prompt the operator (user) to change the speed of the treadmill or the animal to the next test speed based on the testing protocol. In the case of the walkway configuration, the animal is advanced along the walkway at the required speed for the given gait analysis test, while in the case of the treadmill configuration, the treadmill speed is adjusted (manually or automatically) for the given gait analysis test.

Once a complete set of gait analysis data (e.g., plurality of gait cycles) has been collected based on the testing protocol, the system and method end the data collection, the treadmill is stopped and the animal is removed from the treadmill, or the animal is simply removed from the walkway. After the paws are properly identified with adequate number of gait cycles in each of the foregoing tests, the system and method compute the GLS from the measured data using a gait analysis formula, as described herein in greater detail.

This GLS was developed by the present inventor to convey to a clinician and/or owner a degree of impairment of the primary and secondary lame limbs, as well as an amount of compensation absorbed by non-impaired limbs. The GLS enables the presentation of lameness in a simple scale that provides the clinician/owner also with a straight-forward representation of the improvement of lameness as treatment is conducted on the animal.

After computation of the GLS from the raw gait analysis data, the system and method can create a set of reports in paper and/or electronic format. The various reports (paper or electronic) can be configurable. The electronic reports can be delivered over local area networks (LANs) in the clinician's office, over the Internet, or other wired/wireless systems. These electronic reports can include a video showing both the initial exam and comparative reports between initial and current status. These reports can be viewed on a computer connected to the Internet or via a smart device or smart phone.

FIG. 1 illustrates an example system 100 to detect and quantify lameness in animals. The system 100 can include a treadmill configuration that includes a treadmill, or a walkway configuration that includes a walkway. In some embodiments, the system includes a treadmill 102 or walkway 102, as well as a pressure sensor pad 106, and a computing device 108. In other embodiments, additional elements can be included in the system 100, such as one or more cameras 125, a database 126, and a server 130.

In the treadmill configuration, the treadmill 102 includes an electronic/mechanical system (not shown) to control treadmill functionality, such as stop/start, speed and other control functions associated with the treadmill. The treadmill 102 can also include an electronic interface 104 that can interface the computing device 108 with the electronic/mechanical system to enable the computing device 108 to control the foregoing treadmill functionality, and/or other treadmill functionality (e.g., incline/decline).

In either configuration, the treadmill 102 or the walkway 102 can be generally sized and dimensioned (length and width) for different animals. A variety of such treadmills or walkways exist in the marketplace. A certain treadmill or walkway can be selected depending on the breed and size of the animal (e.g., dog), for example.

The pressure sensor pad 106 can be retrofit into the treadmill 102 or walkway 102 or can be integrated/built-in into the treadmill 102 or the walkway 102. In the various embodiments the pressure sensor pad 106 is secured to the treadmill 102 (e.g., between the belt and the bed of the treadmill) or embedded into the walkway 102 so as to remain in place during use of the treadmill 102 or the walkway 102, respectively. The pressure sensor pad 106 can be of any length and width depending on the size/width of the treadmill 102 or the walkway 102.

Moreover, the pressure sensor pad 106 includes a plurality of pressure sensors. The pressure sensors of various densities can be provided for differently-sized animals. The pressure sensor pad 106 communicates gait analysis data from the sensors to the computing system 108, using wireless or wired communication. In the treadmill configuration, the pressure sensor pad 106 can also communicate the gait analysis data through the treadmill's electronic interface 104. The pressure sensor pad 106 can provide gait analysis data concerning the location, pressure and timing as the animal's paws make contact with the pressure sensor pad 106, whether through the belt of the treadmill 102 or the walkway 102. For example, a location can be an X-Y coordinate and pressure can be a Z coordinate. Timing can also be determined by the computing system 108 based on the receipt of X-Y-Z coordinates for various paws from the pressure sensor pad 106.

The computing device 108 interfaces the pressure sensor pad 106 to detect and quantify lameness in animals as described herein, whether in a wireless configuration or a wired configuration. In the treadmill configuration, the computing device 108 can also interface with the treadmill 102, as described herein. The computing device 108 includes an animal registration unit 110, test selection unit 112, treadmill control unit 114 (in the treadmill configuration), data collection unit 116, GLS computation unit 118, report generation unit 120, data store unit 122, and report upload unit 124.

Figures 3, 4A:
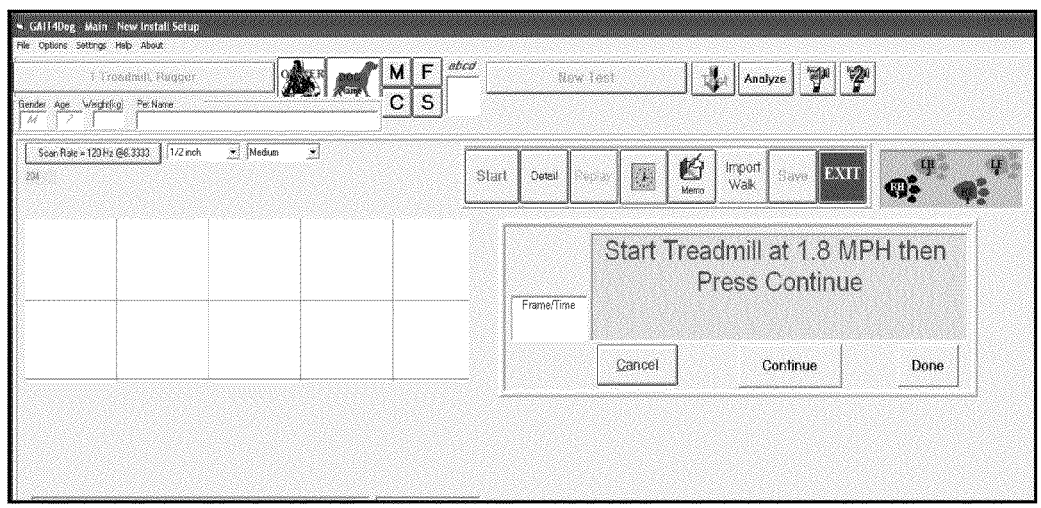
FIG. 3 illustrates an example graphical user interface to register a subject in the system illustrated in FIG. 1.
FIGS. 4A-4C illustrate example graphical user interfaces to select a respective gait analysis test and to set a speed associated with the selected gait analysis test.

The animal registration unit 110 is configured to receive from a user—e.g., via graphical user interface (GUI) or other input device (e.g., dog-tag scanner)—one or more input parameters or characteristics concerning the animal to be tested for lameness. An example GUI is illustrated in FIG. 3, which will be described in greater detail below.

Figure 4B:
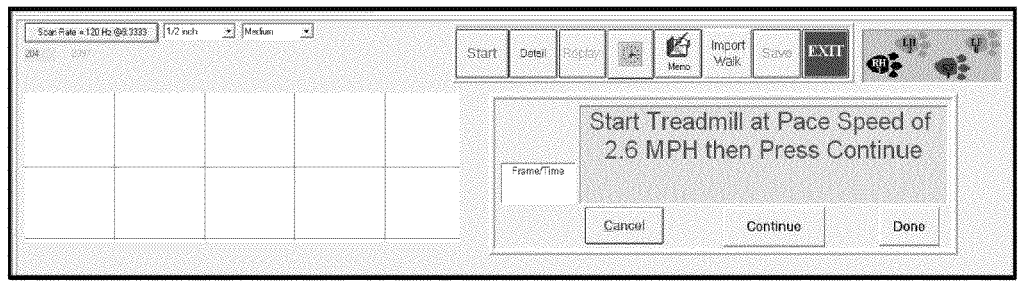
Figure 4C:
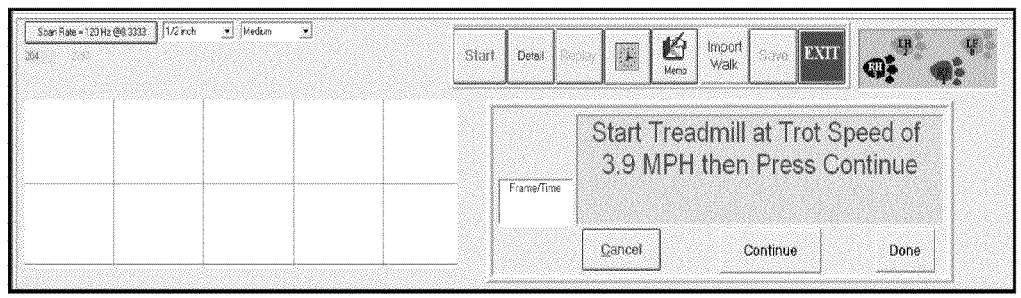

The test selection unit 112 is configured to select an appropriate gait analysis test (e.g., walk, pace trot) in testing an animal (e.g., registered animal) for lameness. In some treadmill embodiments, the test selection unit 112 is enabled via the treadmill control unit 114 to automatically control the treadmill speed corresponding to the gait analysis tests. In other embodiments, a GUI can be provided to prompt the user to manually control the speed of the treadmill 102 or to advance the animal at a particular speed along the walkway 102 for the particular gait analysis test to be performed by the computing device 108. Several example GUIs are illustrated in FIGS. 4A-4C, which will be described in greater detail below.

In the treadmill configuration, the treadmill control unit 114 is configured to enable communication with the treadmill 102 to control its functions (e.g., start, stop, speed, or another function), e.g., as directed by the test selection unit 112. As an example, the treadmill control unit 114 can start the treadmill 102 at the beginning of the testing and stop the treadmill 102 at the end of the testing.

The data collection unit 116 collects gait analysis data associated with gait analysis tests (e.g., walk, pace, trot). The collected gait analysis data can include pressure data, timing data, and location data from the pressure sensor pad 106. Additionally, the data collection unit 116 can also collect video data from the one or more cameras 125.

The GLS computation unit 118 computes a GLS score per limb or leg of the animal, e.g., a dog. As described previously, the GLS score accounts for off and over loading (pressure) and movement for each leg. The GLS score is based on a number of variables derived from a combination of pressure data, timing data, and location data collected while the animal is walking, pacing and/or trotting on the treadmill or the walkway, along with data about the animal such as its breed, height at shoulders and hip, body length and width at shoulders and hip. The computation of the GLS score will be described in greater detail below with reference to FIG. 6.

The report generation unit 120 is configured to create one or more reports on paper and/or electronic formats for one or more lameness testing sessions. The various reports can be configurable based on the data collected and the calculated GLS scores. The report generation unit 120 can deliver the electronic reports to a server 130 or another device over network 128 that is in the clinician's office, over the Internet, or other wired/wireless systems. The electronic reports can include video from the one or more cameras 125. The reports can be for initial or any subsequent lameness testing sessions, as well as comparative reports between one or more lameness testing sessions. These reports can be viewed/received from the server 130 or another device using a computer, smart device, or smart phone via network 128, for example.

The data store unit 122 is configured to store data collected, computed, or generated by the various units 110-120 of the computing device 108 to the database 126, which is connected to the computing device 108. Such connection can we wired or wireless, as well as via the network 128 and/or one or more other networks.

The report upload unit 124 is configured to enable uploading or publication of one or more electronic reports to the server 130 for distribution. The server can include a subscription service.

The one or more cameras 125 are configured to collect video data associated with lameness testing described herein, e.g., for the different gait analysis tests (e.g., walk, pace, trot). The video data can likewise be stored by the data stored unit 122 in the database 126.

As described above, the database 126 is configured to store data collected, computed or generated by various units 110-120 of the computing device 108.

Figure 2:
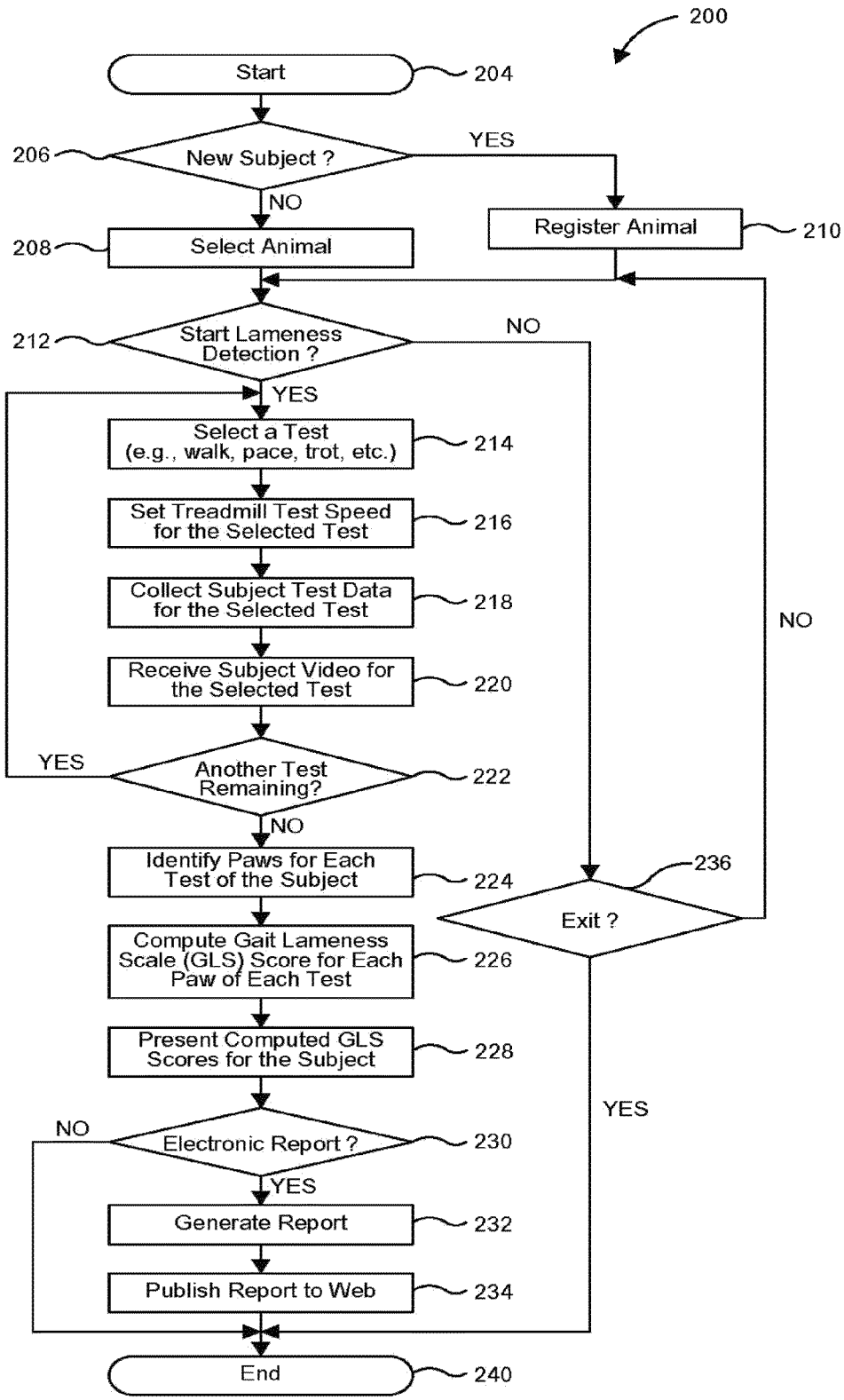
FIG. 2 illustrates an example method of detecting and quantifying lameness in animals that can be practiced using the system illustrated in FIG. 1.

FIG. 2 illustrates an example method 200 of detecting and quantifying lameness in animals that can be practiced using the system illustrated in FIG. 1. The method starts at operation 204.

At operation 206, a determination is made as to whether a new animal or subject (e.g., dog) is to be registered. If it is determined that a new animal is to be registered, the method 210 continues at operation 200 where the animal is registered (e.g., registration record is generated for the animal) and one or more input parameters or characteristics concerning the animal to be tested for lameness are entered in association with the registration. If it is determined that the animal is already registered, then at operation 212 the animal to be tested is selected. For example, search and/or selection capabilities can be provided to retrieve a registered animal to be tested by animal or owner name, registration number, as well as any conventional techniques or other techniques yet to be developed.

At operation 212, a determination is made as to whether to start lameness detection. An example GUI is shown in FIGS. 4A-4C in which a user can hit a start button to start lameness detection. If lameness detection is not started at operation 212, a determination is made at operation 236 as to whether to exit. An example GUI is shown in FIGS. 4A-4C in which a user can hit an exit button to exit. If exit is determined at operation 236, the method 200 ends at operation 240. Alternatively, the method 200 continues at operation 212.

If lameness detection is started at operation 212, a gait analysis test (e.g., walk, pace, or trot) is selected at operation 214. For example, a walk test can be selected. The selection can be automatic or manual by the user as described with reference to FIGS. 4A-4C. At operation 216, the treadmill 102 is set manually or automatically to a certain speed, or the animal is advanced along the walkway 102 at a certain speed, for the gait analysis test selected at operation 214. At operation 218, gait analysis data associated with the subject is collected (or received) for the selected gait analysis test and can be stored to database 126. Collected gait analysis data can be from the operator (user), treadmill 102 or walkway 102, pressure sensor pad 106, as well as any other data to facilitate lameness analysis as described herein. At operation 220, video data is collected (received) from video camera(s) 125 and can likewise be stored to the database 126.

At operation 222, a determination is made as to whether another gait analysis test remains to be performed. For example, it can be determined that a pace and/or a trot gait analysis test may need to be performed. If it is determined that another test remains, the method 200 continues with operations 214-220 until it is determined that no test remains to be completed at operation 222.

Figure 7:
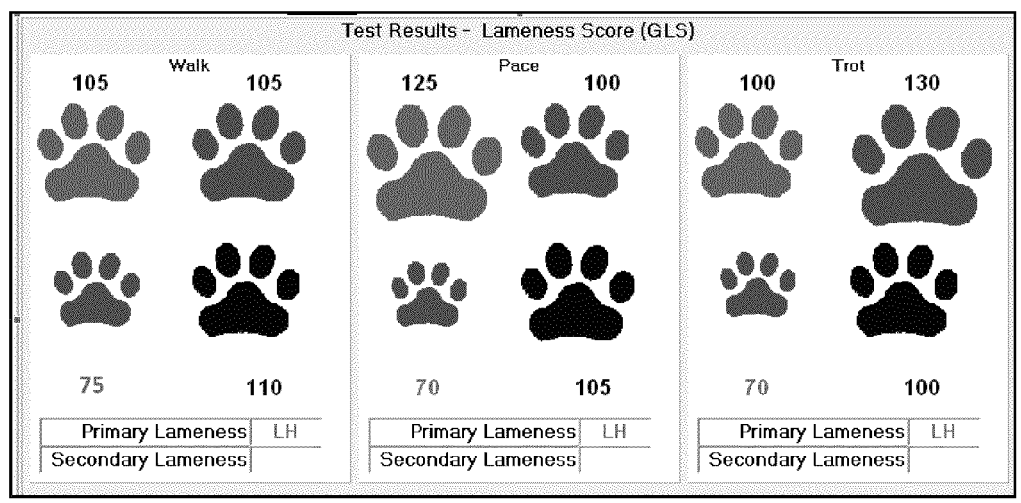
FIG. 7 illustrates a graphical display with a gait lameness scale (GLS) score of each leg in the respective gait analysis tests illustrated in FIGS. 4A-4C.

At operation 224, one or more paws are identified for each of the gait analysis tests (e.g., walk, pace, trot). As described hereinabove, the paws can be identified for each gait cycle of a gait analysis test. At operation 226, the GLS score is computed for each paw identified across the gait cycles in each of the gait analysis tests. The computed GLS scores are presented to show lameness and compensation of the animal's different paws for the different gain analysis tests at operation 228. These scores can be stored to the database 126. An example graphical display is shown in FIG. 7 in which GLS scores are presented for each of the animal's paws resulting from the foregoing gait analysis tests.

At operation 230, a determination is made as to whether to generate an electronic report for the lameness testing of the animal. If report is to be generated, then at operation 232 a current or comparative report is generated based on collected and computed data. Previously computed data can also be retrieved from database 126 for comparative reports, to show improvement or deterioration of the animal over time, using one or more computed GLS scores from one or more previous testing sessions.

At operation 234, the report can be published to the World Wide Web such as uploading/publishing to the server 130. Thereafter, the method 200 ends at operation 240.

FIG. 3 illustrates an example graphical user interface to register a subject in the system illustrated in FIG. 1. For example, various data can be entered or collected for the animal, including subject and/or owner name, birthdate, age, analysis date, gender, weight, anatomical measures or characteristics (e.g., shoulder and hip height/width, body length, leg length) and animal breed.

FIGS. 4A-4C illustrate example graphical user interfaces to select respective gait analysis tests at speeds associated with the selected gait analysis tests. In the treadmill configuration, the treadmill 102 can be set (manually or automatically) to the prescribed speeds, while in the walkway configuration the subject (animal) can be advanced along the walkway at the prescribed speeds. With selection of a start button to begin gait analysis testing, the respective GUIs allow selection of respective gait analysis tests (e.g., walk, pace trot) and collection of gait analysis data of the subject for the respective gait analysis tests from the pressure sensor pad 106, as well as the associated video data of the subject from the one or more cameras 125.

Figure 5:
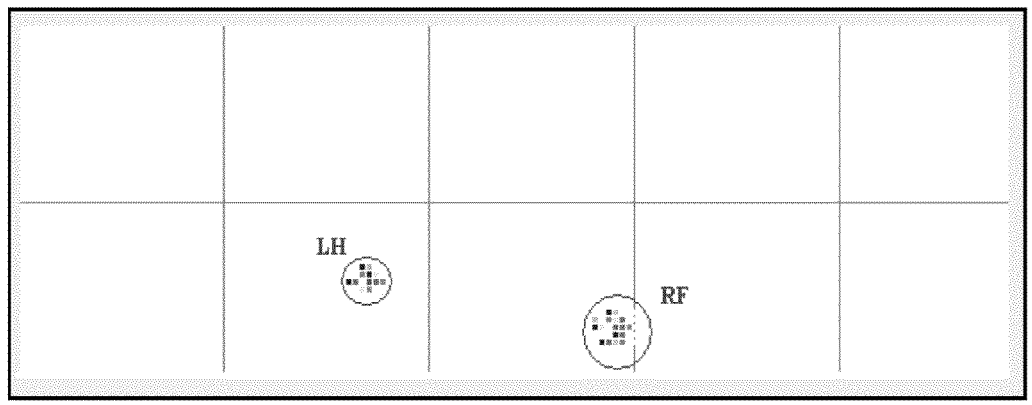
FIG. 5 illustrates an example graphical display that shows multiple activated sensors with associated amounts of pressure exerted by a subject animal on the sensors.

FIG. 5 illustrates an example graphical user interface that shows multiple activated sensors with associated amounts of pressure exerted by a subject (animal) on the sensors of the pressure sensor pad 106. As the animal walks, paces, or trots at an associated speed, the animal normally has three or less paws on the treadmill 102 or the walkway 102 at any given time. In the example shown in FIG. 5, two paws are shown on the treadmill 102 or the walkway 102. The squares, shown in different shades of gray, represent the activated sensors of the pressure sensor pad 106. The squares, which can also be shown in different colors, represent an amount of pressure exerted by the paws (e.g., left hind paw and right forepaw) of the animal on the activated sensors of the pressure sensor pad 106.

For each gait analysis test at the associated speed described above, gait analysis data associated with a plurality of gait cycles (e.g., five or more gait cycles) that are statistically identical are collected, e.g., were each paw is identical to the same paw in each of the gait cycles of the gait analysis test. In various embodiments, a lower or higher number of gait cycles can be applicable. Once the gait analysis data collection is completed, the GLS score for each paw is calculated across the gait cycles of each gait analysis test. An example GLS score computation is described in greater detail below with reference to FIG. 6. A determination of which gait analysis test (speed) produced the worst GLS scores can be determined. The system can retain the GLS scores for all gait analysis tests (speeds) and can graph (e.g., on a GUI and report) a comparison of the GLS scores for a single test set or multiple tests during the treatment regimen (e.g., given date range or since the first testing). An example GLS score by paw for each speed is shown and described below in reference to FIG. 7.

Figure 6:
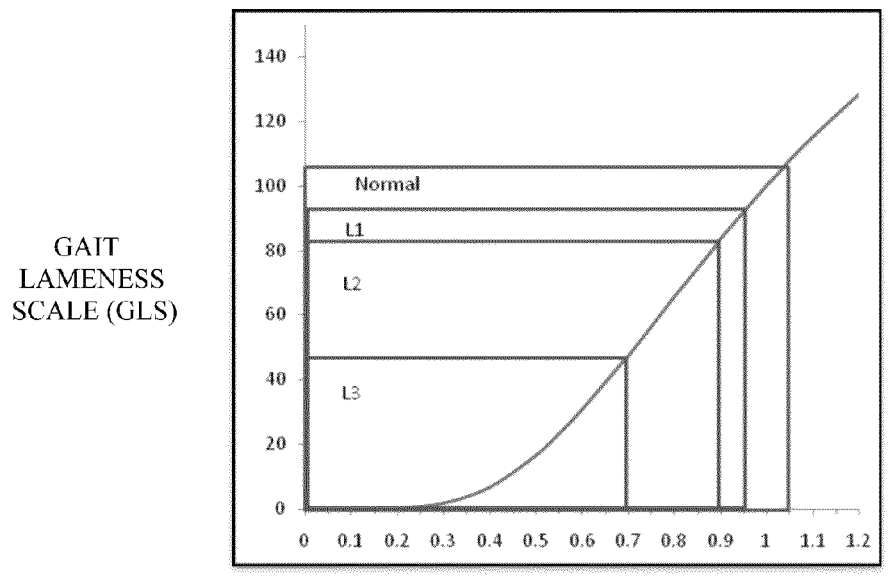
FIG. 6 illustrates a gait lameness scale that provides a measure of lameness for each leg that is specific to a breed of the animal.

FIG. 6 illustrates a gait lameness scale that provides a measure of lameness for each leg that is specific to a breed of the animal. The GLS provides a measure of lameness by leg specific to a breed of the animal (e.g., dog). The GLS is plotted against a total pressure index (TPI) scale to depict how the GLS correlates to the TPI. The TPI was developed and published as a result of research at the Auburn University using an over-the-ground walkway. The TPI was also published in the America Journal of Veterinary Research (AJVR).

The GLS scale is defined such that a score of 100 indicates no lameness (by leg). A score of less than 92 on the GLS scale indicate lameness, wherein the lower the score the greater the lameness. However, scores that are over 108 reflect compensation applied by the animal in a leg due to lameness in a different leg.

The TPI lameness scale currently used in the art by clinicians can be approximated or correlated to the GLS scale as follows: Grade 1 lameness~GLS 83-92; Grade 2 lameness~GLS 47-83; and Grade 3 lameness~GLS less than 47.

A GLS score is determined for each leg using an appropriate gait sample, which includes a plurality of gait cycles. While the primary lameness leg=min(GLS), the secondary lameness leg=min(GLS), having accounted for primary lameness leg. The GLS score is given below:

$$GLS=[(a/\bar{a})+r]$$

In foregoing computation of the GLS score, a=SPI %, $\bar{a}$=mean expected SPI % by breed, r=reach by breed, anatomy and location for a hind paw. SPI is a sensor pressure index as described below. The reach value r is applicable to hind paws and is obtained from a reach lookup table using the following values of b-c; a negative r value indicates lameness of a hind paw and this value is added to the ratio of a/$\bar{a}$ for the hind paw; for all positive r values associated with a hind paw, or if the paw is a forepaw, a zero (0) is added to the ratio of a/$\bar{a}$. Accordingly, the r value is given by:

b=average hind paw location on a side of animal for all cycles; and c=average forepaw location on the same side of animal for all cycles.

The following example illustrates the computation of the GLS score for an example subject (animal) having the following gait analysis data by paw collected for the subject and the breed specific data associated with the subject. In the following example, LF indicates left forepaw, RF indicates right forepaw, LH indicated left hind paw, and RH indicates right hind paw.

TABLE 1

| Gait Cycle | Paw Pressure | | | | Total |
| --- | --- | --- | --- | --- | --- |
| | LF | RF | LH | RH | |
| 1 | 700 | 683 | 333 | 483 | |
| 2 | 689 | 700 | 333 | 488 | |
| 3 | 700 | 706 | 350 | 494 | |
| Total | 2089 | 2089 | 1016 | 1465 | 6659 |

Table 1 illustrates an example gait sample recorded from the pressure sensor pad 106 of the treadmill 102 or the walkway 102, as illustrated in FIG. 1. As illustrated, the gait sample includes three (3) gait cycles. Paw pressure for each respective paw is recorded in each of the gait cycles (e.g., 333 for left hind paw (LF) in cycle 1). A total paw pressure for all gait cycles is computed for each paw (e.g., total of 1016 for left hind paw (LF) in cycles 1-3). Moreover, a total paw pressure is computed for the entire gait sample (e.g., total of 6659 for all paws and all gait cycles).

TABLE 2

| | LF | RF | LH | RH |
| --- | --- | --- | --- | --- |
| SPI % | 31 | 31 | 15 | 22 |
| Mean Expected SPI % | 30 | 30 | 20 | 20 |
| Intermediate GLS Score | 105 | 105 | 76 | 110 |
| (Reach) | 0 | 0 | (1) | 0 |
| Final GLS Score | 105 | 105 | 75 | 110 |

Table 2 illustrates the sensor pressure index percentage (SPI %) indicative of the total paw pressure for all gait cycles divided by total pressure for entire gait sample (all paws and all gait cycles). For example, the SPI % for the left hind paw (LH) is computed as follows: (1016/6659)*100=15.26 (rounded to the hundredth place). The SPI % is rounded to the closest whole number (e.g., 15) for clarity. The mean expected SPI % for the left hind paw by breed of the subject (animal) is given as 20. Accordingly, the intermediate GLS score for the left hind paw, which accounts for the ratio of SPI % and the mean SPI %, is given as 15.26/20*100=76.25. The intermediate GLS score is thus rounded to 76 for clarity.

The final GLS score is obtained by accounting for any negative reach of the hind paws based on the breed, anatomy and location of the paws on the same side of the animal, e.g., average forepaw location for all cycles and average hind paw location for all cycles on the same side of the subject (animal). The negative reach can be obtained by a look-up in a reach lookup table based on the breed and the b-c values, for example. In the foregoing example, the negative reach of the left hind paw (LH) is given as −1. Accordingly, the final GLS score for the left hind paw (LH) is given as 76−1=75.

The final GLS score for the left hind paw of the animal is shown in FIG. 7, first panel, which is associated with the walk test. It should be noted that the GLS scores for the different paws and for the different gait analysis tests (walk, pace, trot), as shown in the different panels in FIG. 7, can be computed in a similar fashion as described hereinabove.

The following GLS computation for a paw equates the GLS computation above to the conventional TPI scale, Grades 1, 2 or 3, using the log norm transformation with mean=0, standard deviation=0.5, as illustrated in FIG. 6:

$$GLS=\log\text{norm}\{[(a/\bar{a})*0.5+(r)*0.5]/75\}*200.$$

In this computation, the variables are similarly given as a=SPI %, $\bar{a}$=mean expected SPI % by breed, and r=reach by breed, anatomy and location for a hind paw. Similarly, r is applicable to hind paws and is obtained from a reach lookup table using the values of b-c.

SPI=Sensor Pressure Index. SPI is the sum of activated sensors by paw, by scan, averaged over scans after filtering minimum contact scans based on treadmill sensor interaction during pressure sensor mat contact, with pressure represented by the switching levels and reported as a scaled pressure value from zero (0) to seven (7) for each sensor. The scale of (0) to (7) can vary depending on the specific type of sensor pad 106 used, with (0) representing no pressure and (7) representing maximum pressure. The SPI % is given below:

$$\text{SPI \%=average}[(\text{SPI by paw/sum of paw SPI})*100]$$
by paw cycle.

The breed specific values are extracted from a breed database. The breed values can be stored in database 126 or in a different database. This breed database can be modified from time to time as new breeds are recognized or more is leaned about a specific breed.

FIG. 7 illustrates a graphical display with a gait lameness scale (GLS) score of each leg in the respective gait analysis tests illustrated in FIGS. 4A-4C. The GLS score can be reported as shown or as a plus or minus number. This is computed by subtracting 100 from the actual GLS score. For example, the GLS score of 80 can be reported as −20 and the GLS score of 140 can be reported as 40.

The foregoing graphical display shows the individual paws in different scales based on the degree of off-loading or over-loading associated with the GLS scores for those paws. The paws, shown in different shades of gray, which can also be shown in different colors, are used to reinforce the differences in the GLS scores. In the example of FIG. 7, the left hind (LH) leg is lame at all speeds. The GLS scores under 100 represent the degree of lameness. The paws with GLS scores above 100 represent a degree to which the particular paw is compensating for the lame leg.

The current system and method provide a unique feature that produces the GLS scores at varying speeds to identify the degree of lameness and compensation. This feature allows the system and method to track progress or lack thereof in treating the animal. The ability to publish this data into appropriate formats for the multitude of computers and smart devices provides unique opportunity for the veterinarian to promote a successful platform and also to promote the veterinarian's services. The combination of the GLS scores with video data creates a simple yet powerful method of communicating the animal's treatment and outcome.

Figure 8:
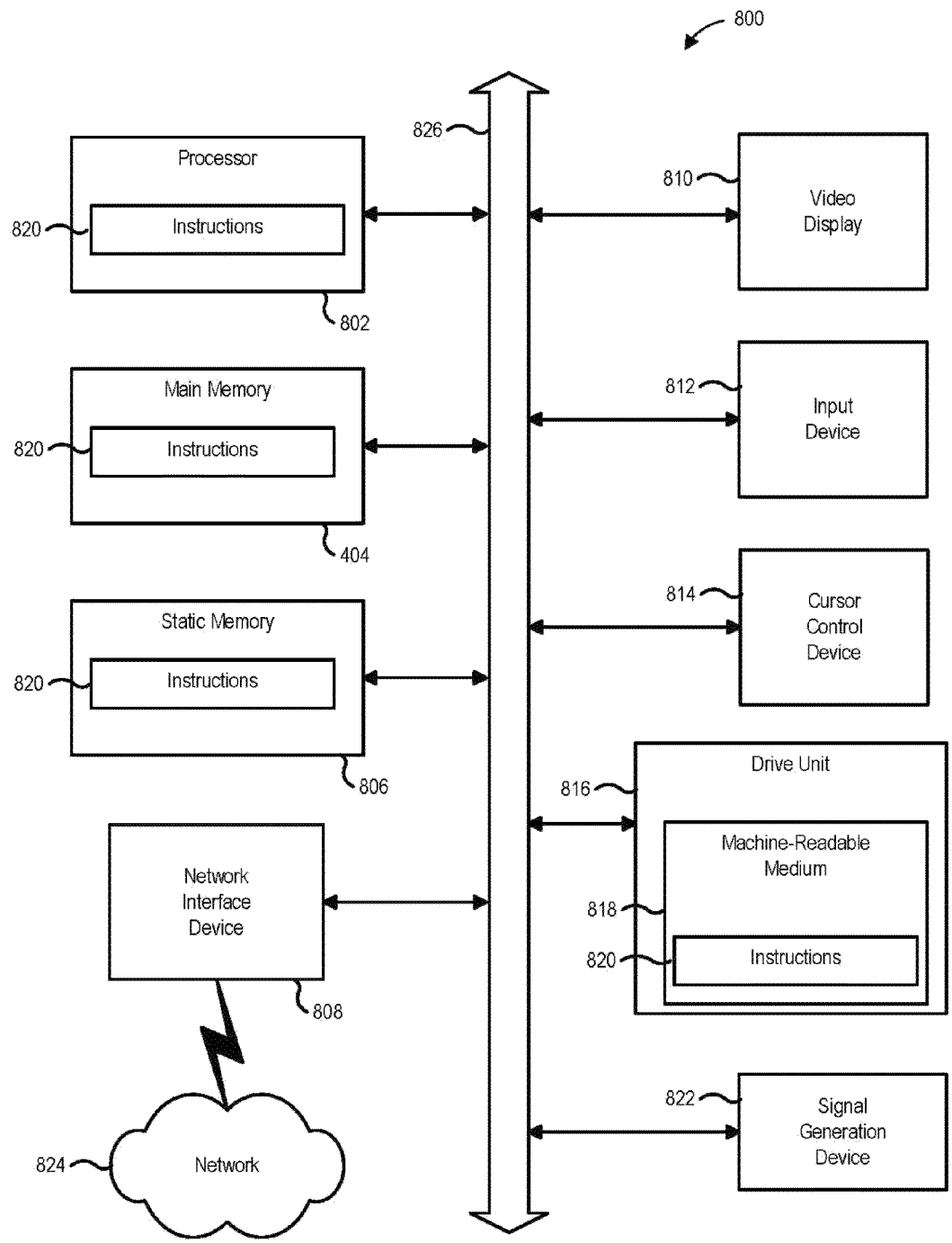
FIG. 8 illustrates a block diagram an illustrative embodiment of a general purpose computer system.

FIG. 8 is a block diagram that illustrates a general computer system 800. The computer system 800 may include a set of instructions that may be executed to cause the computer system 800 to perform any one or more of the computer based functions or methods disclosed herein. The computer system 800, or any portion thereof, may operate as a standalone device or may be connected, e.g., using a network, to other computer systems or peripheral devices, such as described herein, including but not limited to treadmill 102, pressure sensor pad 106, video camera 125, database 126, and server 130.

The computer system 800 may also be implemented as or incorporated into various devices, such as a personal computer (PC), a tablet PC, a personal digital assistant (PDA), a mobile device, a palmtop computer, a laptop computer, a desktop computer, a communications device, a wireless telephone, a land-line telephone, a control system, a camera, a scanner, a facsimile machine, a printer, a pager, a personal trusted device, a web appliance, a network router, switch or bridge, or any other machine capable of executing a set of instructions (sequential or otherwise) that specify actions to be taken by that machine. Further, while a single computer system 800 is illustrated, the term "system" shall also be taken to include any collection of systems or sub-systems that individually or jointly execute a set, or multiple sets, of instructions to perform one or more computer functions.

As illustrated in FIG. 8, the computer system 800 may include a processor 802, e.g., a central processing unit (CPU), a graphics-processing unit (GPU), or both. Moreover, the computer system 800 may include a main memory 804 and a static memory 806 that may communicate with each other via a bus 826. As shown, the computer system 800 may further include a video display unit 810, such as a liquid crystal display (LCD), an organic light emitting diode (OLED), a projection unit, a television, a flat panel display, a solid state display, a cathode ray tube (CRT), or another type of display unit. Additionally, the computer system 800 may include an input device 812, such as a keyboard, and a cursor control device 814, such as a mouse. The computer system 800 may also include a disk drive unit 816, a signal generation device 822, such as a speaker or remote control, and a network interface device 808.

In a particular embodiment, as depicted in FIG. 8, the disk drive unit 816 may include a computer-readable medium 818 in which one or more sets of instructions 820, e.g., software, may be embedded. Further, the instructions 820 may embody one or more of the methods or logic as described herein. In a particular embodiment, the instructions 820 may reside completely, or at least partially, within the main memory 804, the static memory 706, and/or within the processor 802 during execution by the computer system 800. The main memory 804 and the processor 802 also may include computer-readable media.

In an alternative embodiment, dedicated hardware implementations, such as application specific integrated circuits, programmable logic arrays and other hardware devices, may be constructed to implement one or more of the methods described herein. Applications that may include the apparatus and systems of various embodiments may broadly include a variety of electronic and computer systems. One or more embodiments described herein may implement functions using two or more specific interconnected hardware modules or devices with related control and data signals that may be communicated between and through the modules, or as portions of an application-specific integrated circuit. Accordingly, the present system encompasses software, firmware, and hardware implementations.

In accordance with various embodiments, the methods described herein may be implemented by software programs tangibly embodied in a processor-readable medium and may be executed by a processor. Further, in an exemplary, non-limited embodiment, implementations may include distributed processing, component/object distributed processing, and parallel processing. Alternatively, virtual computer system processing may be constructed to implement one or more of the methods or functionality as described herein.

The present application contemplates a computer-readable medium that includes instructions 820 or receives and executes instructions 820 responsive to a propagated signal, so that a device connected to a network 824 may communicate voice, video or data over the network 824. Further, the instructions 820 may be transmitted or received over the network 824 via the network interface device 808.

While the computer-readable medium is shown to be a single medium, the term "computer-readable medium" includes a single medium or multiple media, such as a centralized or distributed database, and/or associated caches and servers that store one or more sets of instructions. The term "computer-readable medium" shall also include any medium that is capable of storing or encoding a set of instructions for execution by a processor or that cause a computer system to perform any one or more of the methods or operations disclosed herein.

In a particular non-limiting, exemplary embodiment, the computer-readable medium may include a solid-state memory such as a memory card or other package that houses one or more non-volatile read-only memories. Further, the computer-readable medium may be a random access memory or other volatile re-writable memory. Additionally, the computer-readable medium may include a magneto-optical or optical medium, such as a disk or tapes or other storage device to capture carrier wave signals such as a signal communicated over a transmission medium. A digital file attachment to an e-mail or other self-contained information archive or set of archives may be considered a medium that is equivalent to a tangible storage medium. Accordingly, the application is considered to include any one or more of a computer-readable medium and other equivalents and successor media, in which data or instructions may be stored.

Although the present application describes components and functions that may be implemented in particular embodiments with reference to particular standards and protocols, the application is not limited to such standards and protocols. Such standards and protocols are periodically superseded by faster or more efficient equivalents having essentially the same functions. Accordingly, replacement standards and protocols having the same or similar functions as those disclosed herein are considered equivalents thereof.

Thus, a system and method to detect and quantify lameness in animals have been described. Although specific example embodiments have been described, it will be evident that various modifications and changes may be made to these embodiments without departing from the broader scope of the invention. Accordingly, the specification and drawings are to be regarded in an illustrative rather than a restrictive sense.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this application. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept. Thus, although specific embodiments have been illustrated and described herein, it should be appreciated that any arrangement calculated to achieve the same purpose may be substituted for the specific embodiments shown. This application is intended to cover any and all adaptations or variations of various embodiments. Combinations of the above embodiments and other embodiments not specifically described herein, will be apparent to those of skill in the art upon reviewing the above description.

The Abstract is provided to comply with 37 C.F.R. §1.72(b) and will allow the reader to quickly ascertain the nature of the technical disclosure of this application. It is submitted with the understanding that it will not be used to interpret or limit the scope or meaning of the claims.

In the foregoing description of the embodiments, various features may be grouped together in a single embodiment for the purpose of streamlining the disclosure of this application. This method of disclosure is not to be interpreted as reflecting that the claimed embodiments have more features than are expressly recited in each claim. Rather, as the following claims reflect, inventive subject matter lies in less than all features of a single disclosed embodiment.

Moreover, it is contemplated that the features or components of various embodiments described herein can be combined into different combinations that are not explicitly enumerated in the foregoing detailed description and that such combinations can similarly stand on their own as separate example embodiments that can be claimed.

The invention claimed is:

1. A method of evaluating lameness in a four-legged animal, the method comprising:
   selecting a gait analysis test associated with a test speed of the animal in relation to a pressure sensor pad having a plurality of sensors;
   collecting gait-related test data associated with the animal at the test speed for a plurality of gait cycles, the gait-related test data being collected in relation to the plurality of sensors of the pressure sensor pad;
   identifying a plurality of paws and associated paw pressure of the animal associated with each of the gait cycles from the gait-related test data; and
   computing a gait lameness score associated with a paw based on a ratio of, a total paw pressure for the paw in the plurality of gait cycles divided by total pressure for the plurality of paws in the plurality gait cycles, and a mean paw pressure for the paw that is expected by a breed of the animal.

2. The method according to claim 1, wherein the gait analysis test is one of a walk test, a pace test, and a trot test.

3. The method according to claim 1, wherein the speed associated with the gait analysis test is related to the breed of the animal.

4. The method according to claim 1, wherein the gait-related test data include pressure data, timing data, and location data of the plurality of paws in relation to the plurality of sensors of the pressure sensor pad.

5. The method according to claim 1, wherein the method further comprises displaying the gait lameness score associated with the paw.

6. The method according to claim 1, wherein the method further comprises:
determining a negative reach value associated with the paw; and
adding the negative reach value to the gait lameness score.

7. The method according to claim 6, wherein the method further comprises displaying the gait lameness score associated with the paw that accounts for the negative reach value.

8. The method according to claim 1, wherein the method further comprises:
iteratively selecting a gait analysis test from a plurality of gait analysis tests, each of the plurality of gait analysis tests associated with a test speed of the animal for walking, pacing, and trotting, respectively; and
performing collecting, identifying, and computing associated with the paw for the gait analysis test selected.

9. The method according to claim 8, wherein the method further comprises displaying gait lameness scores associated with the paw for the plurality of gait analysis tests.

10. The method according to claim 1, wherein the pressure sensor pad is incorporated in one of a treadmill and a walkway.

11. A system to evaluate lameness in a four-legged animal, the system comprising:
a processor; and
a memory storing instructions that, when executed by the processor, cause the processor to perform operations comprising:
selecting a gait analysis test associated with a test speed of the animal in relation to a pressure sensor pad having a plurality of sensors;
collecting gait-related test data associated with the animal at the test speed for a plurality of gait cycles, the gait-related test data being collected in relation to the plurality of sensors of the pressure sensor pad;
identifying a plurality of paws and associated paw pressure of the animal associated with each of the gait cycles from the gait-related test data; and
computing a gait lameness score associated with a paw based on a ratio of, a total paw pressure for the paw in the plurality of gait cycles divided by total pressure for the plurality of paws in the plurality gait cycles, and a mean paw pressure for the paw that is expected by a breed of the animal.

12. The system according to claim 11, wherein the gait analysis test is one of a walk test, a pace test, and a trot test.

13. The system according to claim 11, wherein the speed associated with the gait analysis test is related to the breed of the animal.

14. The system according to claim 11, wherein the gait-related test data include pressure data, timing data, and location data of the plurality of paws in relation to the plurality of sensors of the pressure sensor pad.

15. The system according to claim 11, wherein the operations further comprise displaying the gait lameness score associated with the paw.

16. The system according to claim 11, wherein operations further comprise:
determining a negative reach value associated with the paw; and
adding the negative reach value to the gait lameness score.

17. The system according to claim 16, wherein the operations further comprise displaying the gait lameness score associated with the paw that accounts for the negative reach value.

18. The system according to claim 11, wherein the operations further comprise:
iteratively selecting a gait analysis test from a plurality of gait analysis tests, each of the plurality of gait analysis tests associated with a test speed of the animal for walking, pacing and trotting, respectively; and
performing collecting, identifying, and computing associated with the paw for the gait analysis test selected.

19. The system according to claim 18, wherein the operations further comprise displaying gait lameness scores associated with the paw for the plurality of gait analysis tests.

20. The system according to claim 11, wherein the pressure sensor pad is incorporated in one of a treadmill and a walkway.

21. A computer-readable medium storing instructions that, when executed by the processor, cause the processor to perform operations to evaluate lameness in a four-legged animal, the operations comprising:
selecting a gait analysis test associated with a test speed of the animal in relation to a pressure sensor pad having a plurality of sensors;
collecting gait-related test data associated with the animal at the test speed for a plurality of gait cycles, the gait-related test data being collected in relation to the plurality of sensors of the pressure sensor pad having a plurality of sensors;
identifying a plurality of paws and associated paw pressure of the animal associated with each of the gait cycles from the gait-related test data; and
computing a gait lameness score associated with a paw based on a ratio of, a total paw pressure for the paw in the plurality of gait cycles divided by total pressure for the plurality of paws in the plurality gait cycles, and a mean paw pressure for the paw that is expected by a breed of the animal.

22. The computer-readable medium according to claim 21, wherein the gait analysis test is one of a walk test, a pace test, and a trot test.

23. The computer-readable medium according to claim 21, wherein the speed associated with the gait analysis test is related to the breed of the animal.

24. The computer-readable medium according to claim 21, wherein the gait-related test data include pressure data, timing data, and location data of the plurality of paws in relation to the plurality of sensors of the pressure sensor pad.

25. The computer-readable medium according to claim 21, wherein the operations further comprise displaying the gait lameness score associated with the paw.

26. The computer-readable medium according to claim 21, wherein operations further comprise:
determining a negative reach value associated with the paw; and
adding the negative reach value to the gait lameness score.

27. The computer-readable medium according to claim 26, wherein the operations further comprise displaying the gait lameness score associated with the paw that accounts for the negative reach value.

28. The computer-readable medium according to claim 21, wherein the operations further comprise:
    iteratively selecting a gait analysis test from a plurality of gait analysis tests, each of the plurality of gait analysis tests associated with a test speed of the animal for walking, pacing and trotting, respectively; and
    performing collecting, identifying, and computing associated with the paw for the gait analysis test selected.

29. The computer-readable medium according to claim 28, wherein the operations further comprise displaying gait lameness scores associated with the paw for the plurality of gait analysis tests.

30. The computer-readable medium according to claim 21, wherein the pressure sensor pad is incorporated in one of a treadmill and a walkway.

* * * * *